United States Patent [19]

Oswald et al.

[11] Patent Number: 4,593,141
[45] Date of Patent: Jun. 3, 1986

[54] HYDROFORMYLATION CATALYSIS BY BRANCHED ALKYL DIARYL PHOSPHINE RHODIUM COMPLEXES

[75] Inventors: Alexis A. Oswald, Mountainside, N.J.; Torris G. Jermansen, Staten Island, N.Y.; Andrew A. Westner, Paramus; I-Der Huang, Upper Saddle River, both of N.J.

[73] Assignee: Exxon Research and Engineering Co., Florham Park, N.J.

[21] Appl. No.: 756,564

[22] Filed: Jul. 18, 1985

Related U.S. Application Data

[63] Continuation of Ser. No. 407,050, Aug. 12, 1982, abandoned, which is a continuation-in-part of Ser. No. 120,971, Feb. 12, 1980, abandoned, which is a continuation-in-part of Ser. No. 11,238, Feb. 12, 1979, Pat. No. 4,298,541.

[51] Int. Cl.$^4$ .............................................. C07C 45/50
[52] U.S. Cl. ..................................................... 568/454
[58] Field of Search ..................... 568/454, 909, 451

[56] References Cited

U.S. PATENT DOCUMENTS

| | | | |
|---|---|---|---|
| 3,067,229 | 12/1962 | Feketa | 260/429 R |
| 3,168,553 | 2/1965 | Slaugh | 568/454 |
| 3,239,566 | 4/1968 | Slaugh et al. | 568/454 |
| 3,448,157 | 6/1969 | Slaugh et al. | 568/454 |
| 3,501,403 | 4/1970 | Jacques et al. | 260/429 R |
| 3,511,880 | 5/1970 | Booth | 568/451 |
| 3,517,757 | 6/1970 | Sibert | 568/454 |
| 3,527,809 | 9/1970 | Pruett et al. | 568/454 |
| 3,547,964 | 12/1970 | Oliver | 568/454 |
| 3,560,539 | 2/1971 | Booth | 568/454 |
| 3,644,446 | 2/1972 | Booth | 568/454 |
| 3,660,493 | 10/1967 | Johnson et al. | 568/454 |
| 3,697,600 | 10/1972 | Fenton | 568/487 |
| 3,781,364 | 12/1973 | Fenton | 568/480 |
| 3,801,646 | 4/1974 | Booth | 568/454 |
| 3,818,057 | 6/1974 | Nienburg et al. | 568/454 |
| 3,821,311 | 6/1974 | Hughes | 568/454 |
| 3,825,601 | 7/1974 | Rennick | 568/454 |
| 3,856,837 | 12/1974 | Chandra | 260/429 R |
| 3,857,895 | 12/1974 | Booth | 568/454 |
| 3,917,661 | 11/1975 | Pruett et al. | 568/454 |
| 3,939,188 | 2/1976 | McVicker | 568/454 |
| 3,946,082 | 3/1976 | McVicker | 568/454 |
| 3,965,192 | 6/1976 | Booth | 568/454 |
| 3,968,128 | 7/1976 | McVicker | 260/429 R |
| 4,017,550 | 4/1977 | Kummer | 568/454 |
| 4,041,082 | 8/1977 | Onoda | 568/454 |
| 4,052,461 | 10/1977 | Tinker et al. | 568/454 |
| 4,101,588 | 7/1978 | Nienburg et al. | 568/454 |
| 4,108,905 | 8/1978 | Wilkinson | 568/454 |
| 4,110,404 | 8/1978 | Schaeffer et al. | 568/454 |
| 4,137,240 | 1/1979 | Peterson | 568/454 |
| 4,139,565 | 2/1979 | Unruh | 568/454 |
| 4,143,075 | 3/1979 | Bryant | 568/454 |
| 4,148,830 | 4/1979 | Pruett et al. | 568/454 |
| 4,151,209 | 4/1979 | Paul et al. | 568/454 |
| 4,152,344 | 5/1979 | Unruh | 568/454 |
| 4,215,077 | 7/1980 | Matsumoto et al. | 568/454 |
| 4,230,641 | 10/1980 | Bartish | 568/454 |
| 4,247,486 | 1/1981 | Brewester et al. | 568/451 |
| 4,260,828 | 4/1981 | Morrell et al. | 568/454 |
| 4,283,562 | 8/1981 | Billig et al. | 568/454 |
| 4,287,369 | 9/1981 | Harris et al. | 568/454 |
| 4,287,370 | 9/1981 | Harris et al. | 568/454 |
| 4,298,541 | 11/1981 | Oswald et al. | 568/454 |
| 4,348,539 | 9/1982 | Billig et al. | 568/454 |
| 4,450,299 | 5/1984 | Oswald et al. | 568/454 |
| 4,451,673 | 5/1984 | Oswald et al. | 568/454 |
| 4,454,353 | 6/1984 | Oswald et al. | 568/454 |
| 4,480,137 | 10/1984 | Oswald et al. | 568/454 |
| 4,528,404 | 7/1985 | Oswald et al. | 568/454 |

OTHER PUBLICATIONS

Oswald et al., "Award Symposium on Advances in Synthesis Gas Chemistry", Amer. Chem. Soc., Mar. 18–Apr. 2, 1982.
Falbe, "New Synthesis with Carbon Monoxide" (1980) Springer-Verlag-Berlin, Heidelberg, N.Y.

Primary Examiner—Werren B. Lone
Attorney, Agent, or Firm—R. J. North; E. Thomas Wheelock

[57] ABSTRACT

Branched alkyl diaryl phosphine rhodium carbonyl hydride complexes are surprisingly effective, stable and selective hydroformylation catalysts particularly in the presence of a large excess of t-phosphine ligands. As such, they are advantageously employed as catalysts in a novel low pressure rhodium hydroformylation process producing normal and iso aldehydes by reacting olefins with $H_2$ and CO.

15 Claims, No Drawings

4,593,141

HYDROFORMYLATION CATALYSIS BY BRANCHED ALKYL DIARYL PHOSPHINE RHODIUM COMPLEXES

CROSS-REFERENCE TO RELATED APPLICATIONS

This application is a continuation of application Ser. No. 407,050, filed 8/11/82, which is a continuation-in-part of Ser. No. 120,971, filed Feb. 12, 1980, abandoned which in turn is a continuation-in-part of Ser. No. 11,238 filed Feb. 12, 1979. The parent application was issued as U.S. Pat. No.4,298,541 on Nov. 3, 1981.

FIELD OF THE INVENTION

This invention is related to stable branched alkyl diaryl phosphine rhodium carboyl hydride hydroformylation catalysts for the selective production of aldehydes from olefins. One embodiment of the invention is concerned with the operational and thermal stability of such rhodium complex catalysts in the presence of excess t-phosphine ligands. Another embodiment is concerned with their selectivity for producing normal versus iso aldehydes. A further embodiment describes the effect of the site of branching on the n/i ratio of the products.

BACKGROUND OF THE INVENTION

During the past 15 years, hydroformylation processes catalyzed by t-phosphine rhodium complexes were widely studied. This effort resulted in the commercial development, by Union Carbide Corporation and Davy McKee Ltd., of a continuous, low pressure hydroformylation process based on a triphenyl phosphine rhodium catalyst system. This system is used in several plants worldwide for the production of n-butyraldehyde by reacting propylene with CO and $H_2$. The catalysis chemistry of rhodium hydroformylation was recently published by Oswald et al, in the Petroleum Chemistry Division of the American Chemical Society Preprints (Volume 27, Part 2, pages 292 to 309 in March 1982). It is pointed out in the above journal publication that the commercial triphenyl phosphine rhodium catalyst system has a disadvantage in that it is subject to a slow degradation of the triphenyl phosphine ligand.

Hydroformylation processes catalyzed by rhodium and cobalt complexes were discussed in detail and compared in a recent monograph of Juergen Falbe, New Syntheses with Carbon Monoxide, Springer Verlag, New York, 1980. The first chaper, pages 1 to 222, is on "Hydroformylation Oxo Synthesis Roelen Reaction" by B. Cornils. Cornils concludes that present commercial triphenyl phosphine rhodium complex based processes are not only subject to a slow loss of activity but are suitable only for n-aldehyde production when the reactants are 1-n-olefins. For example, they are unsuitable for the commercial production of i-butyraldehyde.

It was disclosed by Morrell and Sherman in U.S. Pat. No. 4,260,828 that the stability of triphenyl phosphine rhodium carbonyl complex hydroformylation catalyst systems could be improved by the addition $C_1$ to $C_4$ straight chain unsubstituted alkyl diaryl phosphine ligands. However, Morrell considered stability only in the absence of olefin reactants. He expressly excluded from his invention the use of rhodium and alkyl diaryl phosphine ligands alone without triphenyl phosphine.

The present invention is concerned with branched alkyl diaryl phosphine rhodium complex based catalyst systems containing essentially no complexed triphenyl phosphine ligand. In the present hydroformylation process, the use of such catalyst systems, results in improved thermal and operational stability over that of the triphenyl phosphine rhodium complex system. This allows hydroformylation at increased temperature which is particularly important in a continuous operation in which aldehyde products are removed in the vapor phase.

Further, the alpha and beta-branched alkyl derivatives are additionally distinct in providing a lower n/i ratio of aldehyde products i.e., increased selectivity for iso-aldehydes.

The stability of branched alkyl diaryl phosphine rhodium complex based hydroformylation catalyst systems is improved by increasing the concentration of the excess free alkyl diaryl phosphine ligand. This stability improvement is particularly important in continuous hydroformylation. In general, the increasing excess of the ligand generally decreases the rate of hydroformylation. However, this adverse, inhibitory effect of excess ligand is much smaller in the case of the branched than the normal alkyl diaryl phosphines.

SUMMARY OF THE INVENTION

In accordance with this invention there is provided an improved process for the hydroformylation of olefins to produce aldehydes having one more carbon atom than the olefin comprising reacting said olefin with hydrogen and carbon monoxide in a liquid reaction medium which contains a soluble rhodium complex catalyst consisting essentially of rhodium complexed with carbon monoxide and a phosphine ligand and wherein the hydroformylation reaction conditions are controlled to a temperature of from about 90° to about 145° C., or about 50° C. to about 200° C., a total gas pressure of hydrogen, carbon monoxide and olefin of less than about 450 pounds per square inch absolute, or about 16 to about 1015 psia, a carbon monoxide partial pressure of less than about 55 pounds per square inch absolute, or less than about 215 psia, a hydrogen partial pressure of less than about 200 pounds per square inch absolute, or about 65 to about 515 psia, and at least about six total moles of said phosphine ligand for each mole of catalytically-active rhodium metal present in the rhodium complex catalyst or ligand/rhodium molar ratio of about 40 to 3000, wherein the improvement comprises improving the stability of said catalyst against deactivation by employing as said phosphine ligand a phosphine represented by the following formula (I):

$$R_nPPh_{3-n} \qquad (I)$$

wherein R represents a branched chain alkyl group having from 3 to 8 carbon atoms or a cycloalkyl group having from 5 to 12 carbon atoms; n represents 1; and Ph represents phenyl.

Preferred embodiments of the process include wherein said phosphine ligand is present in said liquid reaction medium in an amount of from about 0.25 to about 25 percent, by weight, based on the total weight of the liquid reaction medium; said olefin is an alpha-olefin having from 2 to 5 carbon atoms; including propylene, ethylene or 1-butene; said olefin is an internal olefin, including 2-butene or 2-hexene; said phosphine ligand is a secondary-alkylphenylphosphine wherein the alkyl group has from 3 to 6 carbon atoms, including isopropyldiphenylphosphine and cyclohexylidiphenylphosphine; wherein said catalyst is dissolved in a solvent which comprises the high boiling liquid condensation products of said aldehydes; and wherein the hydroformylation reaction conditions are controlled to a temperature of from about 90° to about 130° C., a total gas pressure of hydrogen, carbon monoxide and olefin of less than about 250 pounds per square inch absolute and a carbon monoxide partial pressue of less than about 30 pounds per square inch absolute.

DESCRIPTION OF THE INVENTION

In particular, the present invention describes a hydroformylation process using branched alkyl diaryl phosphine ligands. This process comprises reacting an olefin with a mixture of carbon monoxide and hydrogen to produce aldehydes, preferably a mixture of normal and iso aldehydes at a temperature between about 80° and about 175° C. under a pressure in the range of 1 and 1000 psi, in the presence of a catalyst system of improved activity maintenance which contains a branched alkyl diaryl phosphine rhodium carbonyl hydride complex catalyst and excess branched alkyl diaryl phosphine ligand.

The branched alkyl diaryl phosphine rhodium carbonyl hydride complex catalysts of the present hydroformylation process contain an unsubstituted or substituted alkyl group with branching in the proximity of the phosphine moiety, i.e., in the alpha and/or beta position. Having such a branched alkyl rather than n-alkyl group leads to a decreased ratio of normal to iso aldehyde products derived from terminal olefins. Also, this branching of the alkyl group produces more effective catalysts and reduces the rate inhibiting effect of the excess branched alkyl diaryl phosphine stabilizer component of the catalyst system.

The aromatic group of the branched alkyl diaryl phosphine ligands can be unsubstituted or substituted. The preferred aryl group is phenyl.

The substituents of the branched alkyl diaryl phosphine ligands as well as the aromatic and aliphatic groups are chemically stable in hydroformylation systems under the conditions of the present process. The rhodium of the catalyst complex is free of halogen, particularly chlorine. Also, the rhodium complex is preferably of a non-chelated character.

HYDROFORMYLATION CATALYST COMPLEX SYSTEMS

The preferred catalyst complex compositions are of the general formula $$[(Ar_2P)_y R^y]_g [Rh(CO)_c H]_s$$

wherein Ar is aryl, preferably an independently selected $C_6$ to $C_{10}$ aromatic unsubstituted or substituted hydrocarbyl radical, more preferably phenyl; $R^y$ is a mono or polyvalent, unsubstituted or substituted alpha and or beta branched alkyl, preferably with $C_3$ to $C_{30}$ carbon atoms; y is the valency of the alkyl groups, preferably in the range of 1 to 4, more preferably 1 or 2; g is the number of branched alkyl diaryl phosphine ligand moieties in the complex, ranging from 1 to 9, preferably 1 to 3; c is the number of coordinated ligands per rhodium, i.e., 1 to 3, preferably 1 or two; s is the number of rhodium carbonyl hydride moieties in a complex molecule, preferably ranging from 1 to 4, most preferably 1.

In the case of the monovalent branched alkyl derivatives the formula of the complex catalysts is the following:

$$(Ar_2PR)_g Rh(CO)_c H$$

wherein g and c are 1 to 3, and g plus c are 3 or 4.

In general, the values of g, c and s are dependent on the coordinative bonding of rhodium.

Preferred substituents of the aromatic groups are $C_1$ to $C_{12}$ alkyl and substituted alkyl, alkoxy, phenoxy, and halogen. These substituents are preferably bound to a phenyl group. Other exemplary aryl groups are naphthyl, furyl, pyrryl, thienyl, pyridyl.

Preferred substituents of the branched aliphatic groups are unsubstituted or substitutedd $C_6$ to $C_{10}$ aryl, a nonhydrocarbyl radical preferably selected from the group consisting of fluorine and organic radicals containing oxygen, sulfur, nitrogen, and phosphorus. The heteroatoms of the organic radicals are preferably of the ether, amine, amide, and phosphine oxide type. The branched alkyl groups are preferably of the secondary alkyl, tertiary alkyl, 2-isoalkyl and neoalkyl type. These types are exemplified by the following branched pentyl groups:

—CH(CH$_3$)CH$_2$CH$_2$CH$_3$  cyclopentyl
—CH$_2$CH(CH$_3$)CH$_2$CH$_3$  —CH$_2$C(CH$_3$)$_3$ In the case of bis-phosphines, the bridging group is preferably a branched alkylene.

Exemplary branched alkyl groups are isopropyl, isobutyl, t-butyl, cyclohexyl, neopentyl, cyclohexylene, cyclohexylene-bis-methyl, benzyl ethyl cyclopentyl, trifluoromethyl cyclohexyl, 2-phenoxymethyl ethyl, trimethylene-bis-2-oxymethylethyl, methine-tris-oxymethyl ethyl.

Exemplary branched alkyl diaryl phosphine ligands are secondary octyl diphenyl phosphine, neopentyl bis-phenoxyphenyl phosphine, cyclohexylene bis-methyl difluoromethylphenyl phosphine, isobutyl bis-chlorophenyl phosphine, tris-diphenylphosphinopropyl phosphine, bis-methoxyphenyl cyclopentyl phosphine.

Further examples of the substituents of the branched alkyl diaryl phosphine ligands of the present invention are given in our copending application, Ser. No. 120,971, and incorporated by reference.

The rhodium carbonyl hydride complex catalysts of the present hydroformylation process are derived starting with the branched alkyl diaryl phosphine ligand. A variety of rhodium compound reactants as disclosed in Ser. No. 120,971 can be used.

In the present hydroformylation process, the catalyst complexes are generated in situ, via the reaction of excess branched alkyl diaryl phosphine ligand and acetylacetonato dicarbonyl rhodium with hydrogen and carbon monoxide. Such a reaction provides the desired branched alkyl diaryl phosphine rhodium carbonyl hydride complexes as indicated by the following reaction scheme:

CH$_3$CO CH$^-$CORh$^+$(CO)$_2$ + Ar$_2$PR $\longrightarrow$

-continued $$[CH_3CO\ CH-CO\ CH_3Rh^+(CO)Ar_2PR]$$

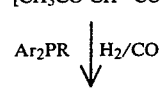

$$(Ar_2PR)_2Rh(CO)H \rightleftarrows (Ar_2PR)_3Rh(CO)H$$

II    I $$(Ar_2PR)_2Rh(CO)_2H \rightleftarrows Ar_2PRh(CO)_2H$$

III    IV

Complexes of formula I–IV are in equilibrium. The major complexes are the coordinatively saturated species I and III. The ratio of I to III is inversely proportional to the CO partial pressure and the steric crowding by the phosphine ligand. The reversible dissociation of complexes I and III, to give the corresponding highly reactive coordinatively unsaturated complexes II and IV, is directly proportional to the temperature and the steric crowding.

The above concept of catalyst complex structures and equilibria were developed via $^{31}P$, $^{13}C$ and $^1H$ nuclear magnetic resonance studies of the type reported in our copending application Ser. No. 120,971. The results of such complex equilibrium studies could be correlated with the results of the hydroformylation process studies. In general, the dicarbonylated complex catalysts led to the formation of major amounts of both normal and iso aldehydes. It is postulated that this is a consequence of the increased steric crowding caused by the branching of the alkyl diaryl phosphine ligands. Thus the branching has a special effect in decreasing the ratio of I to III and thereby decreasing the n/i ratio of products. Since the formation of I is sterically inhibited, branching also reduces the direct effect of excess alkyl diaryl phosphine ligand on forming the unreactive complex I from complex II. Thus the low n/i product ratio and high reactivity of the branched alkyl diaryl phosphine rhodium carbonyl hydride complexes is remarkably maintained in the presence of a large excess of the phosphine ligand.

The main reactive species in such hydroformylations is believed to be complex IV.

The complex catalysts of the present invention could also be prepared via simple ligand exchange. For example, tris-(triphenyl phosphine) rhodium carbonyl hydride was reacted with branched alkyl diaryl phosphines. In such a reaction, stepwise reversible ligand exchange takes place resulting in an equilibrium between the following complexes:

$$(Ph_3P)_3Rh(CO)H \rightleftarrows (Ar_2PR)(Ph_3P)_2Rh(CO)H$$

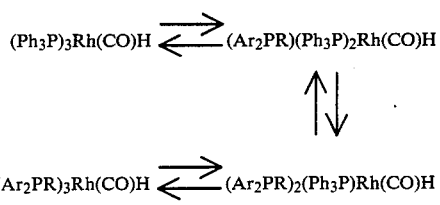

$$(Ar_2PR)_3Rh(CO)H \rightleftarrows (Ar_2PR)_2(Ph_3P)Rh(CO)H$$

Such equilibria could be determined by NMR studies at low temperatures where the rate of reversible ligand exchange is low on the NMR time scale. It was found that a large excess of the branched alkyl diaryl phosphine reactants was required to shift the equilibria and effect complete displacement. This excess was apparently needed to overcome steric inhibiton. It was also observed that the NMR signals of branched alkyl diaryl phosphine complexes were very broad at room temperature. This indicated a rather rapid ligand exchange as a result of the increased dissociation rate of complex I due to steric decompression.

REACTANTS AND PRODUCTS

The olefinic reactants of the present hydroformylation process can be terminally or internally unsaturated and of open chain or cyclic structure. Terminally olefinic reactants, particularly unsubstituted 1-olefins are preferred. Di- and polyolefins can be also employed but should be preferably nonconjugated. Substituted olefinic reactants can be used with the proviso that the substituent will be chemically unreactive in the hydroformylation system and does not interfere with the catalysts. The preferred carbon range of the olefins is $C_2$ to $C_{122}$, preferably $C_3$ to $C_{40}$ more preferably $C_3$ to $C_{12}$ most preferably $C_3$ to $C_8$. More detailed information on the olefin reactants is provided in the grandparent application, Ser. No. 11,238, now U.S. Pat. No. 4,298,541, and the parent application Ser. No. 120,971, both applications being incorporated herein by reference.

Exemplary reactants are propylene, 1-tricosene, 1,4-polybutadiene, 2-butene, cyclopentane, allyl alcohol, trivinyl cyclohexane, acrylonitrile. The olefinic reactant does not have to be employed in the pure state. Olefin mixtures, including different isomers are often preferred. The olefin reactants can also advantageously contain saturated aliphatic hydrocarbons and aromatic hydrocarbons, and non-reactive olefin components as diluents. In a continuous hydroformylation where the aldehyde products are removed in the vapor phase, such volatile diluents, preferably of the $C_1$ to $C_{12}$ carbon range, act as a stripping gas. Examples of such diluents are methane, propane, 2-butene, toluene.

In the case of monosubstituted 1-olefin reactants such as 1-butene, the present hydroformylation process leads to a mixture of normal and iso aldehydes. Such olefin reactants are of the formula $TCH=CH_2$ wherein $TCH=CH_2$ T is $C_1$ to $C_{120}$ unsubstituted or substituted alkyl, T preferably primary alkyl. For example the reactions of allyllic substituted olefins are the following:

$$TCH_2CH=CH_2 + CO + H_2 \xrightarrow{fast} TCH_2CH_2CH_2CHO$$

 

$$TCH=CHCH_3 + CO + H_2 \xrightarrow{slow} TCH_2CH(CH_3)CHO$$

As it is indicated, the side reactions are terminal to internal olefin isomerization followed by slow internal olefin hydroformylation. However, internal olefins can be also hydroformylated in the present process. In this case, the major product is iso aldehyde.

The hydrogen and carbon monoxide reactants are usually employed as a mixture, commonly called synthesis gas. An equimolar mixture of $H_2$ and CO is preferably employed in the present process. However, the process does not depend significantly on the $H_2/CO$ reactant ratios. High $H_2/CO$ ratios of up to 200:1 can be used and preferably about 3:1 without converting the aldehyde products to alcohols. Surprisingly, the present process is not inhibited by high CO pressure. The synthesis gas employed can contain unreactive impurities and/or diluents such as $H_2O$, $CO_2$, $N_2$, and methane. These gases act as a stripping agent in continuous hydroformylation. At high temperatures, some of the hydrogen reacts with the aldehyde products to yield the corresponding alcohols. The latter are often the desired, marketable chemicals.

Hydrogenation of the olefin reactants to yield the corresponding paraffins is usually an undesired side reaction during the present process. Usually, very little olefin hydrogenation occurs. However, the degree of hydrogenation as well as isomerization is directly dependent on the $H_2/CO$ ratio and $H_2$ partial pressure.

Selective rhodium hydroformylation processes in the past were mostly directed for the production of n- rather than i-aldehydes. n-Aldehydes are generally superior as plasticizer intermediates. Rhodium hydroformylation is presently aimed at the production of such intermediates. For example, n-butyraldehyde is being selectively produced as an intermediate for the production of di-2-ethylhexyl phthalate, the single most important plasticizer for polyvinylchloride.

However, the demand for iso-aldehydes as intermediates for other chemicals is increasing. For example, isobutyl and isoamyl alcohols derived from the corresponding iso-aldehydes are important solvents, lube oil additive intermediates and potential gasoline components. Increasing amounts of isobutyraldhyde are used for the production of neopentyl glycol and trimethylol propane intermediates. The latter are used in the production of polyesters. Also, isobutyraldehyde can be converted to methyl methacrylate monomer and methyl isobutyrate gasoline components of high octane value.

The present low pressure hydroformylation process satisfies the increasing demand for isoaldehyde production. Up to now, isoaldehydes were produced only via high pressure processes, mostly using cobalt hydrido carbonyl complex catalyst.

HYDROFORMYLATION PROCESS PARAMETERS AND OPERATIONS

Rhodium complex catalysts are obviously very expensive due to the high cost of rhodium. Therefore, the catalyst complex concentration is usually minimized in rhodium hydroformylation.

The present hydroformylation process is surprisingly attractive for reducing the cost of the rhodium catalyst. Due to the stability of the present catalyst system, no significant losses of the catalyst complex occur. In a continuous process, the aldehyde products can be removed by distillation. The residual solution of the catalyst remains active. Consequently, there is no need for troublesome catalyst recovery via chemical conversions. Also, the addition of the excess branched alkyl diaryl phosphine stabilizer ligand to the rhodium complex catalyst has an exceptionally small inhibition of the activity.

In view of the stability of the present complex catalysts, the selection of the rhodium catalyst concentration in a continuous operation is largely based on investment considerations. At a minimum, the catalyst is used in effective amounts to realize the desired conversion. The concentration of the rhodium complex ranges from 0.001 to 100, more preferably 0.01 to 100, most preferably 0.1 to 10 millimoles rhodium per mole olefin reactant. In a continuous operation, the reactant conversion is largely affected by the rhodium concentration; therefore, amounts in excess of the minimum are often utilized.

In the present catalyst system, 1 to 3 moles of branched alkyl diaryl phosphine ligand is complexed with a rhodium carbonyl hydride moiety. In addition, the catalyst system must contain excess, non-complexed branched alkyl diaryl phosphine in amounts sufficient to maintain the hydroformylation activity. The minimum weight percent concentration of the excess ligand in the reaction medium is preferably 1%, more preferably 10%. Phosphine concentration ranges are 1 to 90, preferably 10 to 80, more preferably 30 to 75%. The mole ratio of excess ligand to rhodium is preferably in the range of about 10 to 10,000, more preferably above 100, most preferably above 400. In general, higher concentrations and ratios preferably above 100 are selected when the desired operation is a continuous rather than a batchwise operation.

In general, ligands of high phosphorus content are preferred to achieve the desired phosphine equivalency by using the minimum weight. Also, when the products are removed by distillation, the phosphine ligands are preferably nonvolatile, i.e., high molecular weight. These two considerations can be satisfied by using bisphosphine or polyphosphine ligands preferably of a non-chelating character.

The present process is operated at low pressures. The total gaseous pressure range is usually between 1 and 1000 psig, more preferably 55 and 500 psig. The temperature range is broad. This reflects the increased stability and reactivity of the catalyst systems. Preferred temperatures range is from 80° to 175° C., more preferably 145° to 175° C. and most preferred temperature range continuous hydroformylations is between 120° and 150° C.

The CO partial pressure is preferably less than 250 psig, more preferably less than 100 psig and most preferably less than 50 psig. The preferred partial pressure of hydrogen is between 50 and 750 psig.

The present process can be carried out either in the liquid or in the gaseous state. The catalyst system can be employed either in a homogeneous solution or deposited as a liquid film on a suitable solid such as silica, alumina, or cross-linked polymer. The preferred process employs a homogeneous liquid reaction phase containing the dissolved catalyst.

The present process does not depend on the use of specific solvents. In general, more polar organic solvents of higher dielectric constant are preferred as long as they possess sufficient solvent power for the olefin and synthesis gas reactants and do not interfere with the stability of the desired catalyst complex species. As such aromatic hydrocarbons are suitable solvents although organic nonhydrocarbon species are preferably used. More preferably, the latter are of a weak, nonsubstituting ligand character. As such oxygenated solvents are preferred. The aldehyde product of the reaction and its oligomers are generally excellent solvents. As a weak ligand, triphenyl phosphine can be used as a solvent component.

Due to the improved stability of the present branched alkyl diaryl phosphine rhodium carbonyl hydride catalysts a continuous mode of operation is often advantageous. When using a homogeneous liquid catalyst system, such an operation can be of a continuous plug flow type including a step for catalyst recovery and then recirculation. Another operation uses a well stirred reactor. A preferred method of catalyst recovery removes the products and unreacted reactants in the vapor phase by a so called product flash-off process. Product flash-off can be carried out directly from the reactor, preferably during hydroformylation. Alternatively, some of the reaction mixture is removed and the product flashed off in a separate vessel usually at a reduced pressure and possibly at a different temperature. The residual catalyst solution is recirculated. A unit can be also operated cyclically for hydroformylation and then product flash-off.

In a preferred continuous hydroformylation product flash-off process, the aldehyde products of the hydroformylation are continuously removed as components of a vapor mixture while the CO, $H_2$ and olefin containing reactant feed is continuously introduced. This process preferably includes the recirculation of most of the unreacted reactants in the gas and/or in the liquid phase. The aldehyde products are preferably condensed and then separated, usually by distillation.

If the continuous product flash-off is all from the reaction vessel, the space velocity of the flash gas stream is appropriately adjusted and additional gas purge is used as required to maintain the volume of the liquid reaction mixture and catalyst activity. Since the rhodium complex is not volatile, no catalyst losses occur. If the phosphine ligand is volatile, additional phosphine is fed to maintain its concentration in the reaction mixture. In such a process, the rate of aldehyde product removal is largely determined by vapor liquid equilibria. These equilibria are highly dependent on the temperature. Consequently, increased hydroformylation temperatures are highly advantageous for effective product removal. This can become critical in the case of less volatile aldehyde products of higher molecular weight. Another adverse factor for product removal from the reaction mixture is high reactant conversion. Since the aldehyde products are much less volatile than the reactants, an aldehyde rich mixture is more difficult to flash off. Increased reaction temperatures are often critical in achieving high reactant conversion and removing the product without an excessive use of unreactive stripping gas.

The liquid reaction mixture of the continuous hydroformylation process contains sufficient dissolved catalyst complex to effect the desired conversion and a sufficient excess of the branched alkyl diaryl phosphine to stabilize the catalyst system. This stabilization results in an excellent activity maintenance. The loss of catalyst activity per day is less than 1%, preferably less than 0.3%.

During continuous product flash-off operation, relatively non-volatile aldehyde oligomer by-products of hydroformylation are enriched in the liquid reaction mixture. These oligomers were discussed in detail in our copending application, Ser. No. 120,971. When a vapor equilibrium is reached, these oligomers are usually major solvent component. Their concentration largely depends on the reaction and/or flash-off temperature.

Using the present catalyst systems of improved thermal stability the application of continuous product flash-off from the reaction mixture can be extended to higher olefins leading to less volatile products. The olefin feeds for continuous product flash-off are in the $C_2$ to $C_{14}$ range, preferably $C_2$–$C_6$, and preferably alpha olefins.

Another preferred method of operation comprises the recirculation of the solution of the present catalyst complex plus excess t-phosphine ligands. In this operation, the reactor is advantageously kept at the elevated pressure and temperature of the hydroformylation. From the reactor, there is a continuous take-off of the reaction mixture of relatively low olefin and synthesis gas concentration. This reaction mixture is then advantageously flashed off at decreased pressure, but increased temperature, in one or more separate vessels. This results in the removal of some, preferably most, of the products. The remaining residual liquid mixture of mainly the catalyst system and trimer is continuously returned to the reactor. Surprisingly, this procedure does not result in significantt catalyst loss or deactivation. The present catalysts are unexpectedly stable not only under hydroformylation conditions but in the absence of olefins and synthesis gas. The complex intermediates of these variable conditions are highly reversible. Consequently, this method can be advantageously applied not only to $C_2$ to $C_6$, but to $C_7$ to $C_{14}$ olefins.

The branched alkyl diaryl phosphine rhodium carbonyl hydride complexes of the present invention are also unexpectedly thermally stable and selective catalysts when the present hydroformylation process is combined with other processes. The present hydroformylation could be advantageously carried out either when coupled with aldol condensation alone or when coupled with aldol condensation and hydrogenation. Such combined processes are highly selective to the corresponding aldehydes. For example, in the case of terminal olefins, such as alpha olefin reactants, the following main aldehyde forming reactions take place when the present silylalkyl diaryl phosphine rhodium complex hydroformylation and hydrogenation catalyst is combined with a base catalyst for aldolization such as KOH.

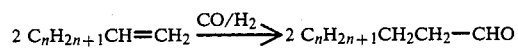

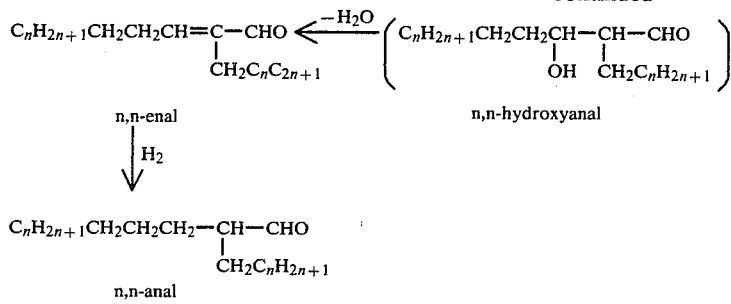

n,n-enal                         n,n-hydroxyanal $$C_nH_{2n+1}CH_2CH_2CH_2-\underset{\underset{CH_2C_nH_{2n+1}}{|}}{CH}-CHO$$

n,n-anal

EXAMPLES

In the following, the practice of the present invention will be illustrated by examples. At first, the preparation of branched alkyl diphenyl phosphines and their properties, particularly basicity, will be discussed. Thereafter, the preparation of the rhodium carbonyl hydride complexes will be discussed, mainly on the basis of NMR ligand exchange studies. Finally, the present hydroformylation process catalysed by branched alkyl diaryl phosphine complexes will be discussed. The emphasis will be on routine, comparative hydroformylation tests including quantitative reaction rate determinations and a complete analysis of the reaction mixtures to determine selectivities to products and by-products. The distinctive characteristics of the present rhodium hydroformylation process using branched alkyl diaryl phosphine ligands over similar processes using different types of phosphine ligands will be shown.

Preparation of Branched Alkyl Diaryl Phosphine Ligands

Some of the volatile branched alkyl diaryl phosphine ligands of the present invention are commercially available. They were purchased as laboratory chemicals and used as such. Other ligands, including novel nonvolatile, branched alkyl diaryl phosphine compounds were prepared during the present work. The various synthetic methods applicable for phosphine ligand preparation are discussed in detail in copending application Ser. No. 120,971. When applying these methods, it is important make sure that the final products are free from reactive secondary phosphine and halogen impurities. Such impurities have an adverse effect on the present catalyst system. Halides presumably lead to objectionable halogen substitution on the rhodium. The treatment of liquid phosphines with 10% aqueous sodium hydroxide solution usually remove the objectionable impurities. The recrystallization of solid phosphines from ethanol was similarly effective.

In the following, the preparation of several branched alkyl diphenyl phosphine ligands is described to illustrate the addition and displacement approaches to their synthesis.

EXAMPLE 1

Neopentyl Diphenyl Phosphine (E-5389-XVII)

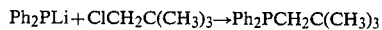

The known, but unavailable, 2,2-dimethylpropyl diphenyl phosphine was derived via reacting 2,2-dimethylpropyl chloride with lithium diphenyl phosphide in a refluxing tetrahydrofuran-hexane solvent mixture. After filtering-off the lithium chloride by-product, the 2,2-dimethylpropyl, i.e., neopentyl diphenyl phosphine, was obtained by the fractional distillation of the filtrate between 109° and 110° C. at 0.1 mm.

EXAMPLE 2

3,3-Dimethylbutyl Diphenyl Phosphine (E-4194,-4214)

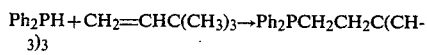

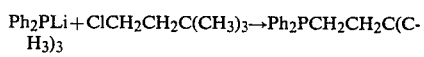

Diphenyl phosphine and t-butylethylene, i.e. 3,3-dimethyl butene, were reacted at 15° C. with ultraviolet light reaction initiation and stirring. However, some phase separation occurred and, consequently, the reaction was slow. The expected adduct was separated from the reactants by fractional distillation. It was obtained as a colorless, clear liquid, boiling between 125°-127° C. at 0.2 mm.

As a known compound, t-butylethyl, i.e., 3,3-dimethylbutyl, diphenyl phosphine, was also synthesized via the known displacement approach: the reaction of lithium diphenyl phosphide with 3,3-dimethylbutyl chloride provided the compound in good yield.

EXAMPLE 3

Cyclopentyl Diphenyl Phosphine (E-4409)

A stirred mixture of 47.6 g (0.7 m) cyclopentene and 136.7 g (0.735 m) diphenyl phosphine in a quartz wessel was irradiated at 15° C. by a broad spectrum ultraviolet light for 17 days. A slow addition reaction took place. Gas chromatographic analysis indicated 60% conversion at the end of the reaction period. The reaction mixture was then fractionally distilled in vacuo to obtain the desired cyclopentyl diphenyl phoshine adduct as a colorless mobile liquid of bp. 138°-140° C. at 0.3 mm (As a by-product, tetraphenyl biphosphine, bp. 210°-212° C. at 0.15 mm, was obtained.)

Calcd. for $C_{17}H_{19}P$: C, 80.29; H, 7.53; P, 12.18. Found: C, 79.98; H, 7.42; P, 12.20.

EXAMPLE 4

1,4-bis-Diphenylphosphinomethyl Cyclohexane (E-5828)

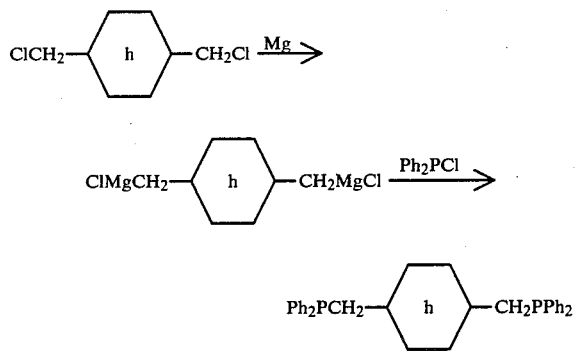

The starting trans-1,4-bis-chloromethyl cyclohexane intermediate reactant was derived from trans-1,4-bis-hydroxymethyl cyclohexane via thionyl chloride chlorination. The Grignard derivative of the latter compound 247.7 g (1.5 m.) was prepared by reacting it with magnesium in refluxing tetrahydrofuran. To the stirred mixture of the Grignard reagent, 724.5 g (3.5 m.) diphenyl chlorophosphine was added in an hour, with ice cooling between 10° and 20° C. Midway through the reactant addition, 2000 ml. toluene solvent was also added to improve the stirring of the gel-like reaction mixture. An analysis of the liquid part of the reaction mixture, after the reactant addition, indicated that the reaction was quantitative.

After the exothermic addition of the diphenyl chlorophosphine, the tetrahydrofuran was removed by distillation. Then 800 ml., 5% aqueous ethylenediamine tetraacetic acid, tetrasodium salt solution was added to the remaining mixture in order to complex and dissolve the magnesium chloride by-product. However, a heterogeneous mixture resulted. This was filtered with suction. Most of the crude bis-phosphine product was obtained as a crystalline filter cake. Some was in the toluene filtrate. The pure product, having an mp. of 162° C., was obtained by recrystallization from toluene.

Basicity of Branched Alkyl Diaryl Phosphine Ligands

The basicity of a number of branched and normal alkyl diphenyl phosphine ligands was studied, primarily to provide data for checking the hypothesis of U.S. Pat. No. 3,527,809 to Pruett et al., regarding a correlation between the activity of t-phosphine rhodium complex hydroformylation catalysts and the basicity of the t-phosphine ligands.

The phosphine basicity determinations via potentiometric titrations were performed according to the method of C. A. Streuli. For reference, see Analytical Chemistry, Vol. 31 pp, 1652 to 1654 in 1959 and Vol. 32, pages 985 to 987 in 1960. Half neutralization potentials (HNP's) of the phosphines were determined using perchloric acid as a titrant and pure nitromethane, free from weakly basic impurities, as a solvent. The values obtained were subtracted from the ΔHNP of the stronger organic base, dipenyl-guanidine, which served as a daily standard reference. The resulting ΔHNP values of the phosphines which were also studied by Streuli, somewhat different ΔHNP values were obtained in the present work. Since ion exchange resin purified nitromethane was used in the present work, the reported values should be more correct than those of Streuli.

Table I lists the relative half neutralization potentials of various alkyl diphenyl phosphines. It is noted that as a group they are much more basic than triphenyl phosphine. The branching of the alkyl group, particularly in the proximity of the phosphorus, further increases the basicity. Therefore, according to Pruett et al. branched alkyl diaryl phosphine ligands would be excluded as ligand candidates for rhodium hydroformylation in his patented process.

TABLE I
Alkyl Diphenyl Phosphine Ligands and Their Basicity

| Example No. | Experimental No. E- | Structure | Indirect Basicity ΔHNP |
|---|---|---|---|
| 7[a] | 4220-II | $Ph_2PCH_2CH_3$ | 363 |
| 8[b] | 4271-I | $Ph_2PCH_2CH_2CH_3$ | 424 |
| 9[a] | 4220-I | $Ph_2PCH_2CH_2CH_2CH_3$ | 404 |
| 10[b] | | $Ph_2PCH_2CH_2CH_2CH_2CH_2CH_3$ | 392 |
| 11[b] | 4244-I | $Ph_2PCHCH_2CH_3$<br>\|<br>$CH_3$ | |
| 12[a] | 4222-V | $Ph_2PC(CH_3)_2$ | 341 |
| 13[c] | 5389-XVII | $Ph_2PCH_2C(CH_3)_3$ | 378 |
| 14[c] | 4214-IX | $Ph_2PCH_2CH_2C(CH_3)_3$ | 412 |
| 15[a] | 4220-III | $Ph_2P\text{—}\langle h \rangle$ | 372 |
| — | Standard | $Ph_3P$ | 510 |

[a] Purchased from Strem Chemicals Inc., Newburyport, Mass.
[b] Purchased from Organometallics Inc., East Hampstead, N.H.
[c] Prepared by reacting lithium diphenyl phosphide with the corresponding alkyl chloride.

Preparation and Properties of Rhodium Carbonyl Hydride Complexes of Branched Alkyl Diaryl Phosphines According to a ligand exchange method particularly useful for NMR studies, branched and normal alkyl diaryl phosphine rhodium carbonyl hydride complexes were prepared by reacting the readily available tris-(triphenyl phosphine) rhodium carbonyl halide (from Engelhard Minerals and Chemicals Corporation, Newark, N.J.) with the corresponding alkyl diaryl phosphine. Generally, the reactions were performed in a 90 to 10 mixtures of toluene and deuterated benzene as a solvent under a nitrogen blanket. The deuterated benzene component was used as a primary NMR standard.

At first, an about 5% solution of the alkyl diaryl phoshine reaction was prepared. To samples of the solution. TPP rhodium carbonyl hydride was added in equivalent and half equivaluent amounts. The resulting mixtures was magnetically stirred until homogeneous liquids were obtained. Additional amounts of the toluene solvent were used if needed. The homogeneous reaction mixture was then studied by $^{31}P$ NMR spectroscopy. Chemical shifts were measured by assigning a shift of 0 ppm to the frequency at which 1M $H_3PO_4$ would resonate.

The $^{31}P$ NMR experiments were carried out using a JEOL FX 90Q multinuclear NMR spectrometer. When required the experimental conditions were adjusted, i.e. the $^1H$-$^{31}P$ decoupling was removed and longer delays between pulses were employed, to determine the relative populations of free and rhodium bound alkyl diphenyl phosphine and TPP.

The results of a systematic $^{31}P$ NMR study of various alkyl diphenyl phosphines are summarized in Table II. The table shows the $^{31}P$ NMR parameters of free and rhodium complexed alkyl diphenyl phosphines in solution at 35° C. An overview of the table indicates that at least five of the seven phosphine ligands examined formed tris-phosphine rhodium carbonyl hydride complexes. Steric crowding apparently inhibited complex formation. Comments on the detailed data of the table are made in the following.

In comparison to n-butyl diphenyl phosphine, secondary butyl diphenyl phosphine is quite ineffective in replacing the TPP ligand (Seq. nos. 1 and 3). Cooling to −60° C. was necessary to observe a clearly resolved doublet signal for the complexed secondary butyl compound. Alternatively, a complex of this ligand could be obtained at room temperature starting with $(Ph_3As)_3Rh(CO)H$ (TPA complex) in place of the TPP complex.

Tertiary butyl and neopentyl diphenyl phosphine (Seq. Nos. 4 and 5) did not form recognizable complexes under standard experimental conditions. However, complex formation was qualitatively shown with a twofold excess of these phosphines as well.

3,3-Dimethylbutyl diphenyl phosphine (Seq. No. 5) exhibited complex forming and equilibration tendencies similar to those of this silicon analog, 2-trimethylsilyl ethyl diphenyl phosphine. Due to the removal of the branching away from the phosphorus, there was no apparent steric inhibition.

Finally, it is noted that cyclohexyl diphenyl phoshine only partially replaced TPP from its complex and exhibited a very high rate of ligand exchange (Seq. No. 8). Overall, this ligand and the secondary butyl diphenyl phosphine and a comparable complexing behavior. In both cases, steric crowding was a severely limiting factor.

Overall, it is apparent that, in spite of their increased basicity, branched alkyl diaryl phosphine ligands are less able to completely replace triphenyl phosphine than normal alkyl diphenyl phosphines. The reason is apparently steric crowding. However, steric crowding is not only inhibiting the multiple coordination of branched alkyl diaryl phosphine ligands to rhodium but is accelerating the dissociation of ligands from coordinatively saturated rhodium complexes. This results in an increased rate of ligand exchange, which is indicated by the broadening of the NMR signals of complexed ligands.

The accelerated dissociation of branched alkyl diaryl phosphine rhodium carbonyl hydride complexes is believed to be responsible for their increased catalytic effectiveness.

TABLE II $^{31}P$ NUCLEAR MAGNETIC RESONANCE PARAMETERS OF FREE AND RHODIUM COMPLEXED ALKYL DIPHENYL PHOSPHINES

| Seq. No. | Chemical Structure of Complex | Chemical Shift σ, ppm Free Ligand | Chemical Shift σ, ppm Complexed Ligand | Coupling Constant JP-Rh Complexed Ligand | Chemical Shift Difference Δσ, ppm Complex- Ligand | Experimental No. E Ligand | Experimental No. E Complex |
|---|---|---|---|---|---|---|---|
| 1 | $(Ph_2PCH_2CH_2CH_2CH_3)_3Rh(CO)H$ | −18.6 | +27.4 | 149 | 46.0 | 4245-IA | 4246-IC |
| 2 | $(Ph_2PCH_2CH_2CH_2CH_2CH_2CH_3)Rh(CO)H$ | −16.8 | +27.6 | 151 | 44.4 | 5404-IIA | 5404IIB&C |
| 3 | $(Ph_2PCHCH_2CH_3)_3Rh(CO)H$ <br> $\|$ <br> $CH_3$ | −4.8 | ∼+40.0 | 154$^{(a)}$ | 45.0 | 4220-IA | 4220-IB |
| 4 | $[Ph_2PC(CH_3)_3]$ | +15.6 | | | | 4220-VA | 4220-VB |
| 5 | $[Ph_2PCH_2C(CH_3)_3]$ | −25.1 | | | | 5389-XXB | 5389-XXC |
| 6 | $[Ph_2PCH_2CH_2C(CH_3)_3]_3Rh(CO)H$ | −16.8 | +27.5 | 152 | 44.3 | 4214-IXA | 4214-IXC |
| 7 | $[Ph_2P$—⟨h⟩—$]_3Rh(CO)H$ | −5.9 | ∼+42.0 | 152$^{(a)}$ | −48 | 4220-IVA | 4220-IIIC |

$^{(a)}$The $^{31}P$—$^{103}Rh$ coupling was not resolved at room temperature but was clearly resolved at −60° C.

Testing of Branced (Alkyl Diaryl Phosphine) Rhodium Complex Based Hydroformylation Catalyst Systems The hydroformylation of butene-1 to provide linear pentanal and branched 2-methyl butanal products was selected for comparative studies of the catalytic properties of branched and normal alkyl diaryl phosphine rhodium carbonyl hydride complexes. The complexes studied were generated in situ. According to a standard method, dicarbonyl acetylacetonato rhodium and the appropriate alkyl diaryl phosphine were used as catalyst precursors. The rhodium carbonyl halide complexes were generated by ligand exchange and hydrogenation during the hydroformylation experiments. Tris-(triphenyl phosphine) rhodium carbonyl hydride in the presence of varying excess of triphenyl phosphine was used as a known catalyst standard for comparison.

The experiments were carried out in 300 ml. autoclaves. The autoclaves were equipped with identical highly effective, impeller type stirrers, operating at 1500 rpm during the experimental runs.

The standard batch hydroformylation was the following: the appropriate amounts of rhodium complex were dissolved in 80 g of the proper mixture of free phosphine and solvent. 2-Propylheptyl valerate or 2-ethylhexyl acetate were used as standard solvents. They were indistinguishable as solvents. Most often, the amount of complex employed provided 100 ppm rhodium concentration. Accordingly, 100 mg. per kg., about 1 mmole per kg. rhodium would be present in 1 kg. starting mixture. The excess ligand added to the solvent was usually 0.14 m., calculated to provide a ligand to rhodium ratio (L/Rh) of about 140.

The 100 g. rhodium complex-ligand solution was placed into the autoclave which was then deaerated by repeated pressurization with nitrogen. The solution under atmospheric nitrogen pressure was then sealed and heated to the reaction temperature, usually 100° C.

When the solution reached 100° C., 20 g. liquid butene was pressured into the autoclave usually with a 1 or 4 or 1 to 5 carbon monoxide-hydrogen initial gas mixture. The butene was followed by the $CO/H_2$ mixture until a pressure of 350 psig was reached. At that point, the supply of 1:4 or 1:5 $CO/H_2$ was shut off and the autoclave was connected to a cylinder of about 1-liter volume containing an about 1:1 $CO/H_2$ feed gas mixture at 1000 psig. The connection was made through a pressure regulating valve set to provide the 1:1 $CO/H_2$ gas to the autoclave to maintain a 350 psig pressure during the reaction. The exact $H_2/CO$ ratio of the feed gas was often varied to maintain the initial $H_2/CO$ ratio in the autoclave. The reaction was typically run to an 80% conversion on the basis of the $H_2/CO$ consumed.

In the early tests, the autoclaves used were equipped with synthesis gas feed lines adjoining the autoclave above the Magnedrive stirred assembly unit (see FIG. 4 of copending application Ser. No. 120,971). It is to be noted that this manner of introducing synthesis gas feed far from the upper level of the liquid reaction mixture (Method A) results in an incomplete equilibration of the synthesis gas mixture between the gas and liquid phase. Particularly in those cases where the initial synthesis gas mixture (used to pressure up the reaction mixture) had a $H_2$ to CO ratio of 10 or higher, the CO component of the subsequent one to one feed gas was not effectively delivered from the top into the liquid reaction mixture due to mass transfer limitations and the reaction mixture was oftened "starved" of CO during the early fast phase of the reaction. As a consequence, the $H_2/CO$ ratio in the liquid temporarily rose to very high values. This resulted in particularly high n- to i-aldehyde product ratios. Also, olefin hydrogenation and isomerization became important side reactions. For comparison, the widely studied tris-TPP rhodium carbonyl hydride catalyst system was used as a standard throughout the work. Generally, the reaction was run to an 80% conversion on the basis of the $H_2/CO$ consumed when using this method.

In the more recent method of operation, the synthesis gas was introduced into the liquid reaction mixture at the bottom, close to the stirrer through a sintered inductor to assure small bubble size and instantaneous mixing (Method C). This method was the best for avoiding higher than equilibrium $H_2/CO$ ratios during the reaction. As such the method gave the smallest n/i ratios of isomeric aldehyde products and the least hydrogenation and isomerization of the olefin, i.e., the highest selectivity for total, i.e., n+i, aldehyde products. Using this method, the reaction was usually run to 50% conversion on the basis of the consumed synthesis gas.

The progress of the hydroformylation was followed on the basis of the amount of 1:1 $CO/H_2$ consumed. The latter was calculated on the basis of the pressure drop in the 1 liter $CO/H_2$ cylinder. Reactant conversion calculated on the basis of CO consumption was plotted against the reaction time to determine the reaction rate. The reaction rate was expressed as the fraction of the theoretical $CO/H_2$ requirement consumed per minute (k min$^{-1}$). At low conversions, the reaction rate remained constant during the reaction if the catalyst system was stable and the olefin isomerization was not excessive. The observed rates showed an excellent correlation with the rhodium concentration. Therefore, rates normalized for 1 m. rhodium concentration could be used to compare catalyst activities.

When the reaction was to be discontinued, the $CO/H_2$ feed valve was shut and the autoclave was immediately cooled with cool water. In case of low conversions, ice bath was used. When cooling was complete, the synthesis gas was released slowly. The residual liquid was visually observed for catalyst decomposition. A dark orange to brown color of the originally yellow mixture indicated increased degrees of catalyst decomposition. Severe catalyst decomposition usually resulted in the precipitation of dark solids.

Analyses of the residual liquid mixture were carried out using gas chromatography. The liquids were analyzed in a gc instrument using a frame ionization detector. By this instrument, the $C_4$ hydrocarbons were detected. Due to the lower response of this detector to the aldehydes, the intensity of the hydrocarbon peaks was multiplied usually by 0.7 to obtain the necessary concentration correction. The individual, gaseous $C_4$ hydrocarbons were separated by another chromatograph. At first, these gases were separated from the liquids and then the individual components of the gas were chromatographed and detected by a thermal conductivity detector.

EXAMPLE 5

Hydroformylation with Various Alkyl Diphenyl Phosphine Rhodium Carbonyl Hydride Catalysts In a series of standard experiments, shown by Table III, various normal and branched alkyl diphenyl phosphine rhodium complex systems were tested as 1-butene hydroformylation catalysts using Method A. It is emphasized that a high temperature, $H_2/CO$ ratios ranging from 4 to 5 and a 140 L/Rh ratio were used in these tests.

Overall, all the n-alkyl diphenyl phosphine complexes exhibited similar catalytic behavior (Seq. Nos. 1-6). At sufficiently elevated temperatures, where they were active and stable, highly linear aldehyde products were selectively produced at a high rate.

In the second group of tests in Table III, the effect of alkyl substituents of different branching was investigated (Seq. Nos. 7-11). Compared to the n-butyl derivative, the secondary butyl derivative was found to be much less selective catalyst for linear aldehyde production (Seq. No. 7). This is an apparent result of the steric inhibition of trisphosphine complex formation.

The last pair of ligands tested showed that minor structural differences result in major differences in the selectivity of the catalyst system. The use of 3,3-dimethylbutyl diphenyl phosphine ligand, the carbon analog of SEP, resulted in high n/i ratio of aldehydes (Seq. Nos. 8 or 9). This ligand shows no steric inhibition in forming the corresponding trisphosphine rhodium complex. In contrast employing a neopentyl group—having one less methylene group between the phosphorus and the sterically demanding t-butyl group—led to a much decreased ratio of normal to iso aldehyde products. This is again a consequence of the steric inhibition of trisphosphine formation.

TABLE III

1—BUTENE HYDROFORMYLATION IN THE PRESENCE OF NORMAL AND ISO (ALKYL DIPHENYL PHOSPHINE) RHODIUM CARBONYL HYDRIDE CATALYSTS

Catalyst: $L_3Rh(CO)H$, L/Rh = 140; Rh = 100 ppm;
Precursor Dicarbonyl Acetylacetonate Rhodium;
Total Pressure 350 psi (26 Atm)

| Seq.* No. | Run No. 7132 | Exp. No. E- | Ligand, L Structure | Reaction Temp., °C. | $H_2/CO$ Ratio Initial | Feed | Final |
|---|---|---|---|---|---|---|---|
| 1 | 118 | 4220-II | $Ph_2PCH_2CH_3$ | 120 | 4.9 | 1.041 | 4.6 |
| 2 | 111 | | | | 4.9 | 1.041 | 2.8 |
| 3 | 119 | 4271-I | $Ph_2PCH_2CH_2CH_3$ | 20 | 4.9 | 1.041 | 3.6 |
| 4 | 122 | | | | 4.9 | 1.041 | 2.6 |
| 5 | 123 | | | | 4.9 | 1.041 | 2.0 |
| 6 | 247 | 4220-I | $Ph_2PCH_2CH_2CH_2CH_3$ | 115 | 4.9 | 1.174 | 3.8 |
| 7 | | 4244-I | $Ph_2PCH(CH_3)C_2H_5$ | 20 | | | |
| 8 | 45 | 4214-IX | $Ph_2PCH_2CH_2C(CH_3)_3$ | 120 | 4 | | 2.7 |
| 9 | 46 | | | | 4 | | |
| 10 | 134 | 5389-XVII | $Ph_2PCH_2C(CH_3)_3$ | 120 | 4.9 | 1.083 | 3.0 |
| 11 | 136 | | | | 4.9 | 1.083 | 2.8 |

| Seq.* No. | Fraction of $H_2/CO$ Reacted Rate Constant k, min$^{-1}$ | Conversion % | Reaction Time Min. | Aldehyde Product Linearity Ratio n/I | $\frac{100n}{n + I \cdot x}$ | Selectivity to Various Compounds, % Aldehyde Products n | I | Butane | 2-Butenes |
|---|---|---|---|---|---|---|---|---|---|
| 1 | 0.045 | 80 | 41 | 8.39 | 89.4 | 75.8 | 9.0 | 9.7 | 5.5 |
| 2 | 0.113 | 80 | 19 | 6.38 | 86.5 | 66.0 | 10.4 | 12.3 | 11.3 |
| 3 | 0.251 | 81 | 10 | 11.57 | 92.1 | 68.4 | 5.9 | 16.9 | 8.8 |
| 4 | 0.326 | 81 | 6.5 | 5.92 | 85.6 | 63.9 | 10.8 | 12.9 | 12.4 |
| 5 | 0.210 | 80 | 55 | 1.92 | 65.8 | 70.0 | 26.0 | 15.6 | 8.5 |
| 6 | 0.337 | 80 | 6.0 | 7.15 | 87.7 | 62.4 | 8.7 | 15.5 | 13.4 |
| 7 | 0.244 | 89 | 15 | 3.14 | 75.86 | | | | |
| 8 | 0.114 | 80 | 15 | 7.57 | 88.3 | 74.3 | 9.8 | 8.6 | 7.4 |
| 9 | 0.285 | 82 | 8 | 6.21 | 86.1 | 70.3 | 11.3 | 8.8 | 9.5 |
| 10 | 0.224 | 81 | 14 | 4.82 | 82.8 | 59.2 | 12.3 | 16.7 | 11.8 |
| 11 | 0.361 | 80 | 6.5 | 3.15 | 75.9 | 53.8 | 17.1 | 7.4 | 21.7 |

*The generally used solvent was 2-propylheptyl valerate. In Seq. No. 6, 2-ethylhexyl acetate was used.

EXAMPLE 6

Hydroformylation with Various Branched Alkyl Diphenyl Phosphine Rhodium Carbonyl Hydride Catalyst Systems In another series of standard experiments, shown by Table IV, various branched alkyl diphenyl phosphine rhodium complex based catalyst systems were tested as 1-butene hydroformylation catalysts using Method C. In these tests, the excess branched alkyl diaryl phosphine ligands were used at two different concentration levels, 0.14 and 1 m. The test temperature was 145° C. The main purpose of the tests was to determine how the site and degree of branching affect the n/i ratio and catalyst activity.

Overall, it was observed in these tests that branching removed from the phosphorus had little effect. For example, the gamma branched ligand (Seq. 2) shows a behaviour similar to that of a straight chain derivative (Seq. No. 2). In contrast, branching on the alpha and beta carbons of the alkyl chain resulted in a reduced ratio of normal to iso aldehydes (Seq. Nos. 5 to 14). Also the reaction rate was unusually high with these compounds at the 1M phosphine excess level (Seq. Nos. 5, 7, 9 and 13). The cyclohexyl diphenyl phosphine—which was not treated to remove harmful impurities i.e. chloride—led to an exceptionally low activity when used at the higher concentration level (Seq. No. 11). The use of impure t-butyldiphenylphosphine, containing chloride, resulted in an unstable, inactive catalyst system. It is reasonably believed that the use of pure t-butyldiphenylphosphine will lead to an active catalyst system.

It was noted that, with the exception of the cyclohexyl diphenyl phosphine, the use of all the alkyl diphenyl phosphine ligands resulted in perfect rate maintenance during the reaction. Plotting the $CO/H_2$ consumption versus the reaction time indicated no change in the rate of hydroformylation.

TABLE IV

EFFECT OF THE BRANCHING OF ALKYL DIPHENYL PHOSPHINE LIGANDS ON THE RATE AND SELECTIVITY OF RHODIUM HYDROFORMYLATION

Reactions at 2500 kPa, with 5 to 1 $H_2/CO$ and 20 g 1-Butene
Plus 80 g Mixture of Alkyl Diphenyl Phosphine Ligand and 2-Ethylhexyl
Acetate Solvent, Using $AcacRh(CO)_2$ as Catalyst Precursor at 145° C.

| | Catalyst System Parameters | | | | $H_2/CO$ Consumption Dependent Factors (50% Conv.) | | | | |
|---|---|---|---|---|---|---|---|---|---|
| Seq. No. | $Ph_2PR$ Structure of —R Group | Ligand Conc. M | Rh Conc. $10^{-3} \times M$ | L/Rh Ratio | $H_2/CO$ Ratio Feed | $H_2/CO$ Ratio Final | Rate Constant K Min$^{-1}$ Normalized 1 m Rh | Found | Time Min. |
| 1 | —$CH_2CH_2CH_2CH_3$ | 1.0 | 0.25 | 4000 | 53/47 | 5.2 | 120 | 0.030 | 23 |
| 2 | | 0.14 | 0.10 | 1400 | 53/47 | 5.5 | 530 | 0.053 | 13 |

TABLE IV-continued
EFFECT OF THE BRANCHING OF ALKYL DIPHENYL PHOSPHINE LIGANDS ON THE RATE AND SELECTIVITY OF RHODIUM HYDROFORMYLATION
Reactions at 2500 kPa, with 5 to 1 $H_2/CO$ and 20 g 1-Butene
Plus 80 g Mixture of Alkyl Diphenyl Phosphine Ligand and 2-Ethylhexyl
Acetate Solvent, Using $AcacRh(CO)_2$ as Catalyst Precursor at 145° C.

| Seq. No. | Ligand | | | | | | | |
|---|---|---|---|---|---|---|---|---|
| 3 | $-CH_2CH_2C(CH_3)_3$ | 1.0 | 0.50 | 2000 | 53/47 | 5.5 | 100 | 0.050* 14* |
| 4 | | 0.14 | 0.10 | 1400 | 53/47 | 5.3 | 490 | 0.049 14 |
| 5 | $-CH_2C(CH_3)_3$ | 1.0 | 0.10 | 10000 | 54/46 | 4.9 | 250 | 0.025 27 |
| 6 | | 0.14 | 0.25 | 560 | 54/46 | 5.0 | 284 | 0.071* 23* |
| 7 | $-CH_2CH(CH_3)_2$ | 1.0 | 0.25 | 4000 | 54/46 | 6.5 | 232 | 0.058 12 |
| 8 | | 0.14 | 0.10 | 1400 | 54/46 | 6.0 | 580 | 0.058 12 |
| 9 | $-CHCH_2CH_3$ ($CH_3$) | 1.0 | 0.20 | 2800 | 53/47 | 5.4 | 220 | 0.044 16 |
| 10 | | 0.14 | 0.05 | 2800 | 53/47 | 5.3 | 460 | 0.023 30 |
| 11 | cyclohexyl | 1.0 | 0.20 | 5000 | 53/47 | 5.3 | 40 | 0.008* 92* |
| 12 | | 0.14 | 0.10 | 1400 | 53/47 | 5.5 | 370 | 0.037* 20* |
| 13 | cyclopentyl | 1.0 | 0.20 | 5000 | 53/47 | 5.4 | 190 | 0.038 18 |
| 14 | | 0.14 | 0.05 | 2800 | 53/47 | 5.5 | 500 | 0.025 27 |

| Seq. No. | n/i Ratio | Aldehyde Linearity $\frac{100n}{n+i}$ % | Selectivities, Mole % | | | | |
|---|---|---|---|---|---|---|---|
| | | | Total | Aldehydes n- | 1- | By-Products 2-Butenes | Butane |
| 1 | 9.6 | 90.5 | 88.7 | 80.3 | 8.4 | 7.8 | 3.5 |
| 2 | 4.2 | 80.8 | 89.1 | 72.0 | 17.1 | 7.8 | 3.1 |
| 3 | 9.8 | 90.7 | 88.6 | 80.4 | 8.2 | 7.9 | 3.5 |
| 4 | 4.4 | 81.6 | 90.4 | 73.7 | 16.7 | 6.9 | 2.7 |
| 5 | 2.6 | 72.5 | 62.9 | 45.6 | 17.3 | 34.7 | 2.4 |
| 6 | 1.7 | 63.4 | 52.7 | 33.4 | 19.3 | 44.5 | 2.8 |
| 7 | 4.4 | 81.6 | 86.8 | 70.8 | 16.0 | 9.6 | 3.6 |
| 8 | 3.3 | 76.9 | 76.5 | 58.8 | 17.7 | 21.0 | 2.5 |
| 9 | 3.4 | 77.2 | 86.5 | 66.8 | 19.7 | 10.5 | 3.0 |
| 10 | 3.2 | 76.2 | 69.3 | 52.8 | 16.5 | 28.1 | 2.6 |
| 11 | 3.6 | 78.2 | 87.5 | 68.4 | 19.1 | 9.4 | 3.1 |
| 12 | 3.2 | 76.2 | 75.4 | 57.5 | 17.9 | 22.0 | 2.6 |
| 13 | 5.4 | 84.5 | 88.1 | 74.4 | 13.7 | 8.4 | 3.5 |
| 14 | 3.4 | 77.1 | 82.2 | 63.4 | 18.8 | 15.0 | 2.8 |

*The rate of reaction was decreasing with time. The initial rate is listed.

EXAMPLE 7

Hydroformylation with a Branched Bis-Phosphine Rhodium Carbonyl Hydride Catalyst System 1,4-Diphenylphosphinomethyl cyclohexane of Example 4 was studied as a branched bis-phosphine ligand for rhodium hydroformylation. As usual, acetylacetonato dicarbonyl rhodium was used as the precursor of the rhodium carbonyl hydride catalyst complex. The rhodium concentration was 0.1 millimole per kg. The phosphine ligand concentration was equivalent to having 0.14 mole phosphine moiety per kg. The conditions of the hydroformylation were the same as in the previous example.

The catalyst was highly effective. The observed rate constant, k $min^{-1}$, was 0.072. This corresponds to a rate constant normalized for 1 m. Rh of 720. The selectivity to total aldehydes was high, i.e. 88.1%. The n/i ratios of aldehydes was 3.2, indicating an increased selectivity for the isovaleraldehyde product.

What is claimed is:

1. In a process for the hydroformylation of a $C_3$ to $C_{40}$ aliphatic, unsubstituted monoolefin to produce an aldehyde having one more carbon atom than the olefin comprising reacting said olefin with hydrogen and carbon monoxide in a liquid reaction medium which contains a $\beta, \beta'$-branched alkylene bis-phosphine rhodium carbonyl hydride complex catalyst and excess $\beta,\beta'$-branched alkylene bisphosphine ligand and wherein the hydroformylation reaction conditions are controlled to a temperature of from about 50° to about 200° C., a total gas pressure of hydrogen, carbon monoxide and olefin of about 16 to about 1015 psia, a carbon monoxide partial pressure of less than 215 psia, a hydrogen partial pressure of about 65 to about 515 psia, and ligand/rhodium molar ratio of about 40 to 3,000, the improvement comprising improving the stability of said catalyst against deactivation by employing said phosphine ligand in excess.

2. A hydroformylation process comprising reacting a $C_3$ to $C_{40}$ aliphatic, unsubstituted monoolefin with carbon monoxide and hydrogen to produce an aldehyde having one more carbon atom than the monoolefin at a temperature between about 80° and 175° C. under a pressure in the range of 1 to 1,000 psi, in the presence of a catalyst system comprising a $\beta$-branched alkyl diaryl phosphine rhodium carbonyl hydride complex catalyst and excess $\beta$-branched alkyl diaryl phosphine ligand to provide a ligand to rhodium ratio ranging from about 10 to about 10,000.

3. A hydroformylation process comprising reacting a $C_3$ to $C_{40}$ aliphatic, unsubstituted monoolefin with carbon monoxide and hydrogen to produce an aldehyde having one carbon more than the monoolefin at a temperature between about 80° and 175° C. under a pressure in the range of 1 and 1000 psi in the presence of a catalyst system comprising β-branched alkyl diaryl phosphine rhodium carbonyl hydride complex catalyst and excess β-branched alkyl diaryl phosphine ligand to provide a ligand to rhodium ratio between 10 and 10,000 wherein the complex is of the formula:

$$((Ar_2P)_yR^y)_gRh(CO)_cH$$

and wherein Ar is a $C_6$ to $C_{10}$ aryl, $R^y$ is a mono-, di-, tri-, or tetravalent β-branched $C_4$ to $C_{30}$ alkyl, y is 1 to 4, g is 1 to 3 and c is 1 to 3.

4. The process of claim 3 wherein y is 1 and s is 1.

5. The process of claim 3 wherein y is 2 to 4 and the complex is non-chelated.

6. The process of claim 3 wherein y is 2 and s is 1.

7. The process of claim 3 wherein c is 2.

8. The process of claim 3 wherein said β-branched alkyl is a 2-isoalkyl group.

9. The process of clim 3 wherein said β-branched alkyl is a neoalkyl group.

10. The process of claim 3 wherein said phosphine ligand is a non-chelating branched alkylene bis-phosphine of the formula

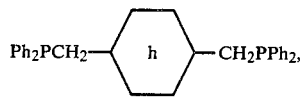

wherein Ph represents a phenyl group.

11. A hydroformylation process comprising reacting a $C_3$ to $C_{40}$ aliphatic, unsubstituted monoolefin with carbon monoxide and hydrogen to produce an aldehyde having one more carbon atom than the monoolefin at a temperature between about 80° to 175° C. under a pressure in the range of about 1 to about 1,000 psi in the presence of a catalyst system comprising a branched alkyl diaryl phosphine rhodium carbonyl hydride complex catalyst of the general formula $$(Ar_2PR)_gRh(CO)_cH$$

wherein Ar is $C_6$ to $C_{10}$ aryl, R is a $C_4$ to $C_{30}$ β-branched alkyl, g and c are 1 to 3 and g plus c are 3 or 4 and which contains excess branched alkyl diaryl phosphine ligand to provide a ligand to rhodium ratio of about 10 to 10,000.

12. The process of claim 11 wherein said β-branched alkyl is a 2-isoalkyl group and c is 1 or 2.

13. The process of claim 11 wherein said β-branched alkyl is a neoalkyl and c is 2.

14. A hydroformylation process comprising reacting 1-butene with carbon monoxide and hydrogen to produce n- and i-valeraldehydes at a temperature between about 80° to 175° C. under a pressure of about 1 to 1,000 psi in the presence of a catalyst system comprising a neopentyldiphenyl phosphine rhodium carbonyl hydride complex catalyst and excess neopentyldiphenyl phosphine to provide a ligand to rhodium ratio of about 10 to 10,000.

15. A hydroformylation process comprising reacting 1-butene with carbon monoxide and hydrogen to produce n- and i-valeraldehydes at a temperature between about 80° to 175° C. under a pressure of about 1 to 1,000 psi in the presence of a catalyst system comprising a 1,4-bis(diphenylphosphinomethyl)cyclohexane rhodium carbonyl hydride complex catalyst and excess 1,4-bis(diphenylphosphinomethyl)cyclohexane to provide a ligand to rhodium ratio of about 40 to 3,000.

* * * * *